United States Patent [19]

Whiting et al.

[11] Patent Number: 4,509,368

[45] Date of Patent: Apr. 9, 1985

[54] ULTRASOUND TOMOGRAPHY

[75] Inventors: James F. Whiting, Indooroopilly; Rolf H. L. Koch, Bardon, both of Australia

[73] Assignee: The Commonwealth of Australia, Australian Capital Territory, Australia

[21] Appl. No.: 467,481

[22] PCT Filed: Jun. 18, 1982

[86] PCT No.: PCT/AU82/00098

§ 371 Date: Feb. 17, 1983

§ 102(e) Date: Feb. 17, 1983

[87] PCT Pub. No.: WO83/00009

PCT Pub. Date: Jan. 6, 1983

[30] Foreign Application Priority Data

Jun. 22, 1981 [AU] Australia ............................... PE9381

[51] Int. Cl.$^3$ ............................................. G01N 29/04
[52] U.S. Cl. ......................................... 73/624; 73/625; 73/628; 73/633; 128/660
[58] Field of Search ................. 73/597, 599, 626, 625, 73/624, 628, 633, 634; 128/660

[56] References Cited

U.S. PATENT DOCUMENTS

| 3,990,300 | 11/1976 | Kossoff | 73/626 |
| 4,074,564 | 2/1978 | Anderson | 73/606 |
| 4,105,018 | 8/1978 | Greenleaf et al. | 73/597 |
| 4,222,274 | 9/1980 | Johnson | 73/626 |
| 4,279,157 | 7/1981 | Schomberg et al. | 73/626 |
| 4,338,948 | 7/1982 | Perez-Mendez et al. | 128/660 |

Primary Examiner—Anthony V. Ciarlante
Attorney, Agent, or Firm—Cushman, Darby & Cushman

[57] ABSTRACT

A method and apparatus for ultrasound tomography for use in clinical diagnostics, the apparatus comprising paired couples of transmission transducers (3) and reflection transducers (5,6), the paired couples of transducer means being independently operable within a container (1) of ultrasound transmission medium to provide data capable of processing by computational methods for mathematical reconstruction of the distribution of specific values of acoustic data to permit separate comparative and synergistic examinations of the data thus obtained to classify the internal structure of a body.

10 Claims, 1 Drawing Figure

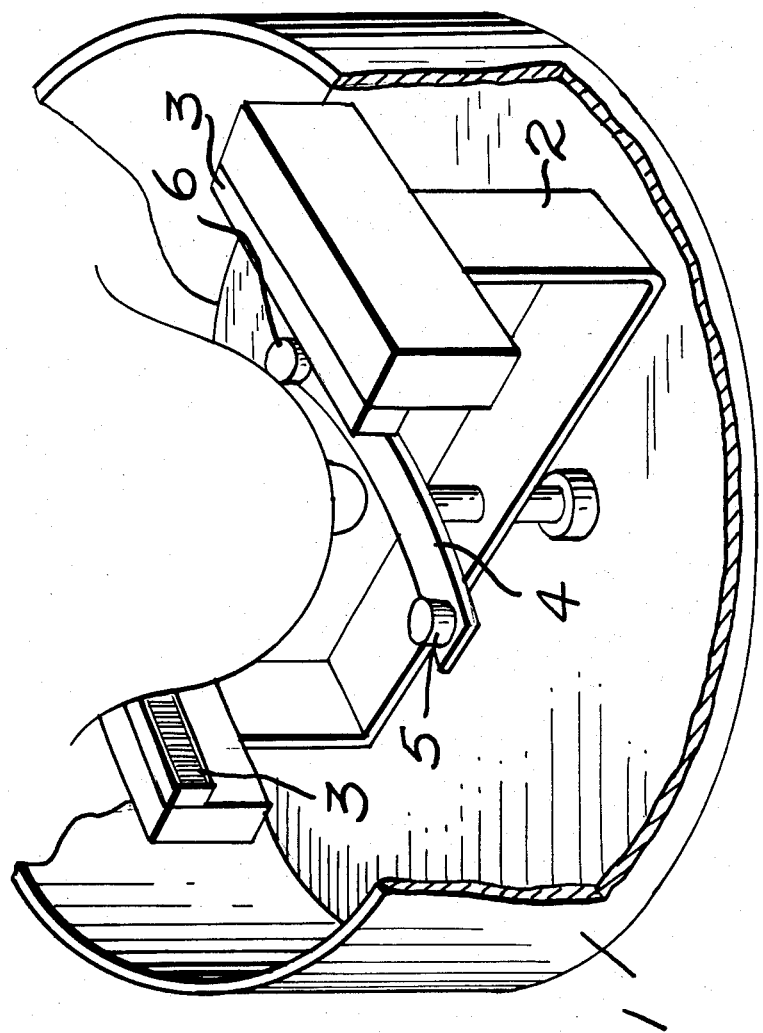

ULTRASOUND TOMOGRAPHY

This invention relates to improvements in methods and apparatus for ultrasound tomography, particularly although not exclusively suitable for clinical diagnostics.

Generally speaking non-invasive examination techniques are preferred in humans or other animals to alleviate the risks associated with anaesthetics, infection etc. inherent in surgical techniques. In inanimate bodies, non-destructive examination techniques are preferred from the point of view of cost and practicality. X-ray and gamma-ray techniques have proven effective in obtaining accurate imagery of the internal structures of bodies but of recent years, the use of non-ionizing radiation on animals, particularly humans, is preferred. It is significant to note that those parts of the body which are highly susceptible to radiation damage also statistically show a predisposition to formation of cancers, cysts and other lesions. In a patient suspected of suffering a lesion of the abovementioned kind it is important to conduct regular examinations of the affected region to monitor any changes in the lesion. In women, it is recommended that breast examination be carried out on a regular basis in view of the high incidence of breast cancers.

To accommodate the need for non-invasive examination techniques without the use of ionizing radiation, certain ultrasonic examination and imaging techniques have been developed. These techniques employ levels of ultrasonic energy below those known to be harmful to biological tissues. Although known ultrasound systems have provided information useful in clinical diagnostics, they are not entirely satisfactory in terms of resolution and reproducability of the type and quality of data obtained.

Essentially there are two types of ultrasound imaging systems presently available. These rely on echo reflection information or transmission information for the reconstruction of images representing the internal structure of a body.

At present, the most highly developed and thus most used system is the pulse echo B-scan mode, or variants thereof. In this system an ultrasonic pulse, reflected from a surface or interface within a medium, is detected and represented on a video display with the strength or amplitude of the return echo modulating the brightness of the display. The relative positions of the pulsing-/receiving transducer and the reflecting surface are displayed on a video screen in the X and Y axis. In a composite image comprising a plurality of echo signals obtained from scans at different angles within a given plane in a body, the resultant video representation is presented as an image in which each picture element or pixel has a direct geometrical positional relationship to the various reflecting interfaces associated with the body.

The B-scan system is subject to a number of disadvantages resulting from its use of the pulse-echo mode. As the echoes are generated at interfaces between media of different acoustic impedance within a medium, weak reflected signals from some delicate tissue structures may not be detected, particularly after further attenuation in the medium on the reflected signal path. Unless the angle of impingement of a pulse is substantially perpendicular to a reflecting surface or interface, the detected strength of the reflected pulse will be severely attenuated. This makes calibration of such apparatus difficult or impossible due to movement of various parts of the patient's body during breathing, heartbeat etc.

Recent developments in B-scan techniques however have alleviated certain of its inherent shortcomings to some extent. In a manner analogous to X-ray computerized tomography, images representing acoustic impedance distributions within a medium can be reconstructed and displayed as a two dimensional image on a video screen. Acquired data relating to a plurality of tomographic images in the same specimen may then be translated to give a fairly crude three dimensional representation of impedance distributions within the body under examination.

Further improvements in ultrasound image construction have been postulated by the reconstruction of speed distributions in a two dimensional plane using computerized transmission or time-of-flight tomography. As used herein, the expression "transmission tomography" refers to acoustic speed or acoustic attenuation or a combination thereof. Receiving transducers are arranged in an arcuate array for receiving pulses transmitted in a fan beam array. The arcuate receiving array detects the arrival of a pulse which is transmitted in a substantially fan shaped divergent beam and each of the receivers detects portion of the pulse travelling along a particular path through the specimen. In this manner the speed distribution along each path can be determined and the information thus obtained can be mathematically reconstructed as an image on a video screen.

Generally speaking pulse echo tomography is employed to scan the sagittal and transverse planes of soft tissues such as female breasts. The sagittal plane extends from front to back (or vice versa) of a human body longitudinally thereof whilst the transverse plane is perpendicular thereto extending between the sides of the body. Transmission tomography is generally limited to portions of the body wherein transmitting and receiving transducers are alignable on either side thereof. In breast examination, transmission tomography is generally used to examine tissue in a coronal plane which is perpendicular to both the sagittal and transverse planes.

In any of the above techniques, certain assumptions and allowances should be made in computational methods of reconstruction of images. Amongst these, the distribution and variation of refractive indices in various tissue samples should be taken into account, and diffraction effects should also be taken into account as well as difficulties arising from phase interference caused by the arrival at the transducer of wavefronts from multiple directions. Computational methods which aim to take into account such phenomena in computer reconstructions of acquired data have not increased accuracy significantly.

Fan beam geometry has been considered preferable to parallel beam geometry as the latter generally requires both a translational and rotational movement relative to a specimen to obtain sufficient data to permit accurate image reconstruction. As both the translational and rotational motions require mechanical linkages (usually controlled by stepping motors) certain inaccuracies are inherent in measurement due to mechanical inaccuracies, machine tolerances, backlash etc. Fan beam arrays in transmission tomography overcome to some extent such inaccuracies by the obviation of the translational motion otherwise required but reconstruction of images thus obtained is penalised by longer computation time.

Although linear transducer arrays have hitherto been used in pulse-echo tomography, their use in transmission tomography has not been known. In co-pending Australian Patent Application No. 46107/79 and Australian Pat. No. 487,477, both in the name of the present applicant, the construction of linear array transducers for pulse-echo tomography is described. Amongst the various advantages accruing from linear transducer arrays is the ability to focus the beam electronically by sequential energization of the elements comprising the array. Additional focussing can be obtained by the use of a cylindrical lens or mirror or a curved surface on the transducer array.

The present invention aims to overcome or alleviate the problems of prior art ultrasound imaging techniques and to provide a rapid, more reliable technique for non-invasive ultrasound diagnostics.

It is considered that significant improvements in both speed and accuracy of data acquisition can be obtained in transmission tomography by employing one or more substantially parallel pairs of spaced linear arrays of transmitter and receiver transducers.

It is further considered that significant improvements in acoustic tomographic techniques can be obtained by synergistically combining transmission tomography data with reflection tomography data and mathematically reconstructing images thus obtained.

According to one aspect of the invention there is provided an apparatus for transmission tomography comprising:

a scan means including at least one ultrasonic energy transmitter means;

at least one ultrasonic energy receiver means, said transmitter means and said receiver means comprising linear transducer arrays coupled in spaced substantially parallel relationship to respectively transmit and receive substantially parallel beams of ultrasonic radiation through a selected plane in a body.

Preferably said transmitter means and said receiver means are adapted for rotation within a medium for transmission of ultrasonic energy.

Preferably said apparatus includes means to selectively pulse individual transducers comprising said linear transducer arrays.

Preferably said apparatus includes means to selectively rotate said scan means.

Preferably said apparatus is adapted to permit selective relative axial movement between said scan means and said body.

Preferably said apparatus includes a computation means for mathematical reconstruction of specific values of acoustic speed at a plurality of positions within said body.

Preferably said apparatus includes a computation means for mathematical reconstruction of specific values of acoustic attenuation at a plurality of positions within said body.

Preferably said apparatus includes computation means for mathematical reconstruction of specific values of acoustic speed and acoustic attenuation at a plurality of positions within said body.

Preferably said apparatus includes means for visual display of said mathematically reconstructed specific values.

Preferably said means for visual display comprises means for simultaneously displaying both the acoustic speed data and the acoustic attenuation data as separate, adjacent or superimposed images of the structure of correlated planes of said body.

According to a further aspect of the invention there is provided an acoustic tomography apparatus comprising a transmission tomography scanning means in combination with a reflection tomography scanning means, said reflection tomography scanning means comprising:

means for transmission of ultrasonic energy and means for reception of reflected ultrasonic signals.

Preferably the acoustic tomography scanning means includes means for determining the magnitude, amplitude or time-of-flight of the reflected signals, and the direction of radiation paths for transmission and reflection.

Preferably the acoustic tomography scanning means includes means for selectively rotating said reflection tomography scanning means.

Preferably the apparatus includes means to permit selective relative axial movement between said reflection tomography scanning means and said body.

Preferably the apparatus includes means for correlating transmission tomography data and reflection tomography data.

Preferably the apparatus includes means for visual display of said transmission tomography data and reflection tomography data as separate, adjacent or superimposed images.

Preferably the apparatus includes means for computation of tomographic data to obtain a characterization of the material comprising said body.

Preferably the transmission tomography apparatus comprises linear transducer arrays coupled in spaced substantially parallel relationship to produce substantially parallel beams of radiation.

Preferably said acoustic tomography scanning means is so adapted and arranged whereby transmission data is obtained in a coronal plane of said body and reflection data is obtained in a plane perpendicular thereto, said means for correlating transmission and reflection tomography data providing means for reconstruction of an image in a coronal plane of said body.

Alternatively, the transmission tomography apparatus comprises transducer arrays arranged and coupled to produce a fan shaped beam of radiation.

According to another aspect of the invention there is provided a method for examining and classifying the internal structure and composition of a body comprising the steps of:

(a) transmitting acoustic radiation through a plane of said body with substantially parallel beams of radiation;

(b) receiving said substantially parallel beams of radiation; and (c) mathematically reconstructing by computational means specific values of acoustic transmission data so received for displaying as one or more visual images.

According to yet a further aspect of the invention there is provided a method for examining and classifying the internal structure and composition of a body comprising the steps of:

(a) transmitting acoustic radiation through said body along a plurality of selected directions;

(b) measuring the time-of-flight or attenuation of acoustic waves or a combination thereof after propagating through the body;

(c) use of computational methods for processing the data thus acquired to mathematically reconstruct the distribution of specific values of acoustic transmission data at a plurality of points within the said body;

(d) additionally measuring the arrival time, magnitude or amplitude and directions of back-scattered reflected acoustic waves after reflection from structures on and in the said body.

Preferably the method further includes the step of simultaneously displaying both the specific values of transmission data and the reflection data as separate and/or adjacent and/or superimposed images or representations of the internal structure of correlated planes of the said body.

Preferably the method further includes the step of separate, comparative and synergistic examinations of the transmission data and reflection data to classify the internal structure of the said body.

Preferably the method further includes the step of simultaneously displaying both the specific values of transmission data and reconstructed values of the reflection data from a plurality of points in the same plane of the said body in separate and/or adjacent and/or superimposed images or representations of the internal structure of the same plane of the said body.

Preferably the method further includes the step of simultaneously displaying both the specific values of transmission data at a plurality of points within the said body and the reflection data from the body's outside borders in superimposed images or representations of the internal structure and the outside border of the same plane of the said body.

There are a number of different scanner arrangements for acoustic tomography apparatus but possibly the most widely used scanner arrangement at the present time comprises:

1. A tank for containing an acoustic radiation propagation medium, usually water;
2. A frame mounted within the tank for axial rotation;
3. Electroacoustic transducers mounted on one or both ends of the frame which is movable to describe a circular path coaxial with the tank when the frame is rotated;
4. Suitable circuitry to control pulsing of the transmitting transducer (s) and circuitry to direct reflection or transmission signals from receiving transducers to data acquisition and processing apparatus such as computers.

The signal generating and receiving transducers can be arranged in an arcuate array with a radius of curvature centred on the axis of rotation or the transmitting transducer. The array may comprise alternate transmitters and receivers or a single, central transmitter with an arcuate array of receivers on either side.

Scanners for transmission tomography apparatus may comprise a single transmitter transducer arranged to transmit fan shaped beams of radiation. The receiver transducers (usually arranged at a similar distance from the axis of rotation as the transmitter receivers) are arranged either in an arcuate or linear array.

A particularly preferred embodiment of the present invention differs in one aspect from prior transmission methods and apparatus whereby the abovementioned computational errors and those arising from scanning by mechanical translation may be alleviated in transmission tomography by means of substantially parallel linear transducer arrays whereby the beams of transmitted ultrasonic energy are substantially parallel. A further benefit to be gained from such an arrangement is that the mathematical reconstruction of images from transmission signals thus obtained is considerably simpler and consequently significantly faster. As in prior art methods and apparatus the rotatable frame supporting the transmitters and receivers is rotated in a stepwise fashion through predetermined angles of rotation and with the present invention, during the periods of rest, the specimen under examination is insonated by substantially parallel beams of radiation.

The linear arrays may be energized in any desired manner and in particular, the insonating beam may be electronically and/or otherwise focussed to improve the data quality and consequently reconstructed image quality. It is considered that beam focussing enhances image accuracy due to a reduction in refraction and phase interference effects in an irregularly shaped, acoustically inhomogeneous specimen such as biological tissue.

It is expected that by experiment and through subsequent comparison with histological results that significantly more geometrically accurate images are obtainably by insonation with parallel beams of ultrasonic radiation.

In a particularly preferred embodiment of the invention, the apparatus comprises a tank of approximately 600 mm in diameter and a volumetric capacity of approximately 100 liters. The rotatable support frame comprises a centrally supported beam with coupled pairs of linear transducer arrays comprising 192 transducers each with a width of 1 mm and a height of 15 mm. The transducer arrays are separated by a distance of 200 mm. The operating frequency of the transmitter transducers is preferably 5 MHz but clinically acceptable results may be obtained over a frequency range of 1 MHz to 15 MHz. The rotatable frame is suitably rotated through angles of arc of multiples of 0.45° by stepping motor coupled to the data acquisition circuitry. After completing at least 180°, preferably 360° of arc the rotatable frame is returned to its initial position and axial adjustment of the frame may then be accomplished by the control circuitry to permit examination of further planes of interest within the specimen under examination. The scanning cycle for each step of rotation is typically 1 second. Other arrangements of transducer arrays which are considered to be suitable may be selected from arrays comprising 64-512 transducers, each with a width of 0.3-3 mm and a height of 2-20 mm.

The time-of-flight and/or transmission attenuation data or a combination thereof thus acquired is processed in a computer with angular orientation information by any one of a number of known computational methods to provide reconstructions of structural features of the specimen under examination. The reconstructions may be presented as numerical data but preferably are displayed on a video screen as a two dimensional image within a selected plane either as grey scale or coloured pixels representing the spatial distribution of structural features of the specimen under examination.

By employing the principles of the simple, substantially parallel pairs of coupled linear arrays of transducers as described above it would be possible to construct "stacked" arrays whereby a number of planes may be investigated simultaneously, thus further reducing computation time and translational errors arising from mechanical translation between planes of interest. In a further variation of the above embodiment, two-dimensional arrays of transducers may be employed to permit even wider selectivity in either choice of orientation of investigational planes, beam focussing or simultaneous investigation in a plurality of planes. Coupled pairs of transmitter/receiver transducers may also be arranged with substantially perpendicular irradiating axes, the pairs being energized with the same or different frequencies.

The above described method and apparatus is particularly suitable for examination of soft tissue body components such as female breasts.

The present invention also contemplates improvements in both transmission and reflection tomography techniques by a synergistic combination of various tomographic techniques. Such combinations may include:
1. Time-of-flight transmission tomography with attenuation transmission tomography;
2. B-scan mode tomography with time-of-flight transmission tomography;
3. B-scan mode tomography with attenuation transmission tomography;
4. B-scan mode tomography with time-of-flight and attenuation transmission tomography;
5. Time-of-flight transmission tomography with boundary echo information;
6. Attenuation transmission tomography with boundary echo information;
7. Time-of-flight and attenuation transmission tomography with boundary echo information.

Either of combination 1–7 above may comprise linear or fan arrays of transducers.

By combining various transmission tomography techniques with various B-scan or other echo techniques, it is considered that a synergistic effect is obtained on the accuracy, reliability and reproducability of results obtained. Data acquired by each scanning apparatus may be simultaneously displayed on one or more video screens as separate and/or adjacent and/or superimposed images. Such separate data may be compared for common regions within a body and computed to give a classification of the material in selected common regions according to known data.

The apparatus for the above described combination techniques may suitably comprise at least one coupled pair of transmission transducers arranged for scanning in a selected plane within a specimen and at least one echo reflection scanner arranged to scan in the same plane or a different plane of the specimen. The orientations of the transmission scanner apparatus and the reflection scanner apparatus may be fixed relative to each other or independently operable to selectively scan through a variety of planes within the specimen under examination.

One such arrangement is schematically illustrated in the accompanying drawing. A tank 1 of suitable dimensions contains therewithin a rotatable frame 2 with linear transducer arrays 3 mounted in spaced substantially parallel relationship for transmission tomography. A further frame 4 is mounted for co-rotation or independent rotation coaxially with frame 2. A transmitter transducer 5 and a receiver transducer 6 are mounted adjacent the ends of frame 4 for pulse-echo tomography. Transmitter and receiver transducers 5 and 6 are preferably pivotally mounted on frame 4 and their respective "sights" may be controlled individually or in coupled fashion. Preferably transducers 5 and 6 are adapted to oscillate as a couple through a predetermined angle range and at a predetermined rate. Frames 2 and 4 are associated with the same or different stepping motors (not shown) for stepwise rotation within the tank through selected angles of arc. The tank is filled with a suitable ultrasound propagating medium such as water and in use is situated beneath a known patient supporting couch. Height adjustment means (not shown) is provided for relative movement between the apparatus and the tissue specimen under examination to permit examination in different planes.

It is considered that in the various aspects of the present invention significantly more accurate quantitative and qualitative two-dimensional and three-dimensional images of the structure of a specimen may be obtained than otherwise hitherto possible.

It will be appreciated by a skilled addressee that many modifications and variations may be made to the various aspects of the present invention without departing from the spirit and scope thereof.

We claim:

1. An apparatus for examining the internal structure of a body along mutually perpendicular planes of interest, comprising:
means for transmitting pulses of ultrasonic energy through said body along a plurality of substantially parallel paths in a first plane;
means for receiving ultrasonic energy pulses transmitted through said body in said first plane;
means for transmitting pulses of ultrasonic energy into said body along a second plane perpendicular to said first plane;
means for receiving ultrasonic energy pulses reflected by said body along said second plane;
and means for correlating acoustic transmission and reflection data for reconstruction of one or more images corresponding to said first plane.

2. An apparatus as claimed in claim 1 wherein said means for correlating acoustic transmission and reflection data comprises means for mathematically reconstructing by computational means specific values of said acoustic transmission and reflection data for display as one or more visual images.

3. An apparatus as claimed in claim 1 wherein said means for correlating acoustic transmission and reflection data is adapted to measure time-of-flight of energy pulses transmitted through said body.

4. An apparatus as claimed in claim 1 wherein said means for correlating acoustic transmission and reflection data includes means for visual display of separate reconstructed images corresponding to said first plane or an image combining said transmission and reflection data.

5. An apparatus for examining the internal structure of a body along mutually perpendicular planes of interest, comprising:
opposed respective linear arrays of transducers for transmitting and receiving pulses of acoustic energy through a body in a first plane; transducer means for transmitting in a second plane perpendicular to said first plane acoustic energy pulses into said body; transducer means for receiving signals reflected by said body in said second plane;
and computation means for reconstructing received transmitted and reflected acoustic signals as a visual image on a display means, said image corresponding to a plane of interest coincident with said first plane;

and means to selectively pulse individual transducers comprising said linear array for transmitting pulses of acoustic energy along substantially parallel paths.

6. An apparatus as claimed in claim 5 wherein said opposed linear arrays of transducers are adapted to rotate relative to said transducer means operative in said second plane.

7. An apparatus as claimed in claim 5 wherein said opposed linear arrays of transducers and said transducer means operative in said second plane are both rotatable relative to said body.

8. A method for examining and classifying the internal structure and composition of a body, comprising;
transmitting through said body from a first linear array of transducers acoustic radiation with substantially parallel beams of radiation in a first plane;
receiving acoustic signals transmitted through said body at a second linear array of transducers arranged substantially parallel to and in the same plane as said first array;
recording the time of flight of acoustic signals transmitted through said body as transmission data;
transmitting to said body through a second plane perpendicular to said first plane acoustic signals and receiving signals reflected from said body and recording said reflected signals as reflection data;
mathematically reconstructing by computational means specific values of transmission and reflection for display as one or more visual images of a plane of interest in said body coincident with said first plane.

9. A method as claimed in claim 8 wherein the transmission and reflection data is displayed as separate, adjacent or combined images representative of a single plane of interest in said body.

10. A method as claimed in claim 8 wherein reflection data is recorded as time-of-flight data or amplitude attenuation data.

* * * * *